United States Patent [19]

Schaar

[11] 4,158,363
[45] Jun. 19, 1979

[54] DIAPER WITH EXTENSIBLE FASTENER

[75] Inventor: Charles H. Schaar, Lake Zurich, Ill.

[73] Assignee: Colgate-Palmolive Company, New York, N.Y.

[21] Appl. No.: 880,260

[22] Filed: Feb. 22, 1978

Related U.S. Application Data

[63] Continuation of Ser. No. 752,495, Dec. 20, 1976, abandoned.

[51] Int. Cl.² ............................................. A61F 13/16
[52] U.S. Cl. ............................ 128/287; 128/DIG. 30
[58] Field of Search ....................... 128/284, 286, 287; 24/67 AR, 73 VA

[56] References Cited

U.S. PATENT DOCUMENTS

| 3,930,503 | 1/1976 | Tritsch | 128/284 |
| 3,983,876 | 10/1976 | Cepuritis | 128/284 |
| 3,985,136 | 10/1976 | Cepuritis | 128/284 |
| 3,987,793 | 10/1976 | Milnamow | 128/284 |
| 3,989,047 | 11/1976 | Cepuritis et al. | 128/284 |
| 3,999,544 | 12/1976 | Feldman et al. | 128/284 |
| 4,014,339 | 3/1977 | Tritsch | 128/284 |
| 4,024,867 | 5/1977 | Mesek | 128/284 |

FOREIGN PATENT DOCUMENTS 1441567 7/1976 United Kingdom ................ 24/73 VA Primary Examiner—Robert W. Michell
Assistant Examiner—C. F. Rosenbaum
Attorney, Agent, or Firm—Powell L. Sprunger

[57] ABSTRACT

A disposable diaper comprising, an absorbent pad assembly, a release sheet on a surface of the pad assembly adjacent a side edge, a tape strip having a first portion secured to the surface of the pad assembly, a securement portion releasably attached to the release sheet, and an extensible central portion connecting the first and securement portions.

6 Claims, 15 Drawing Figures

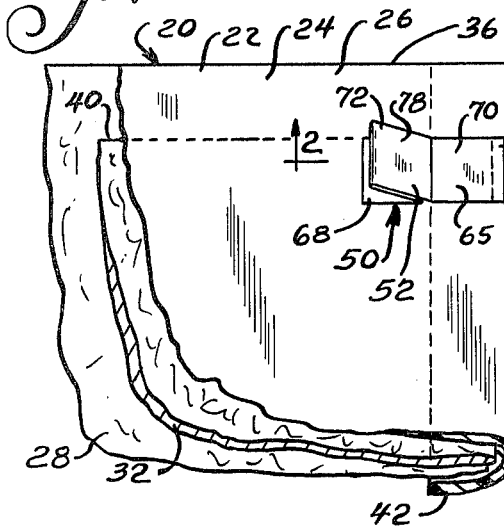
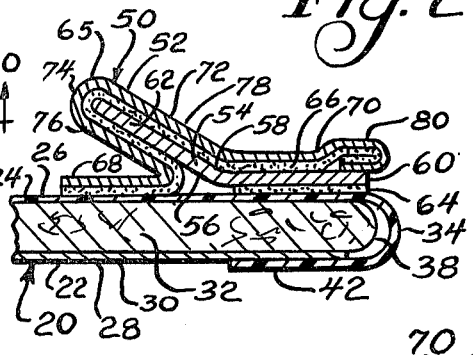
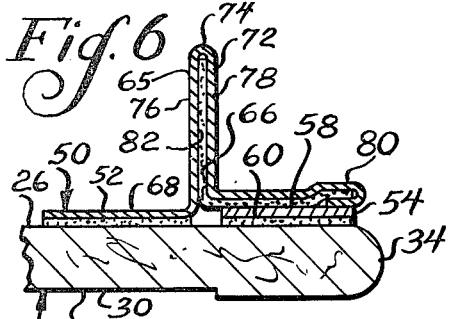
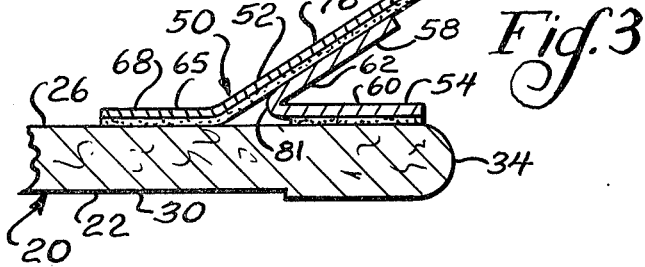
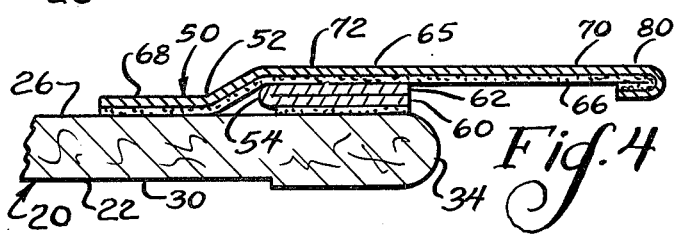
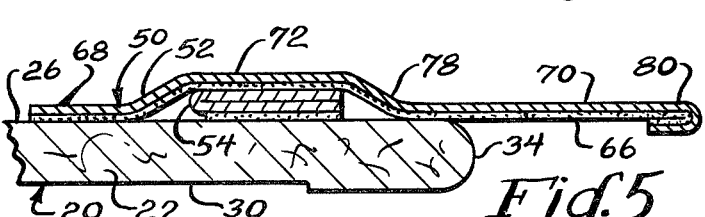
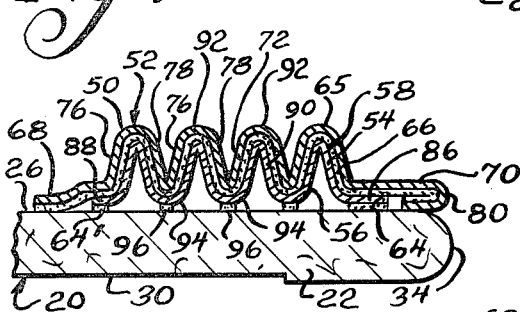
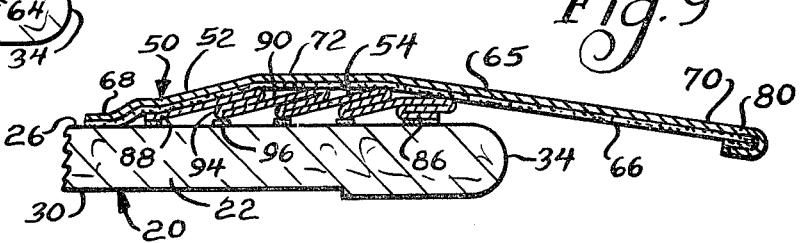

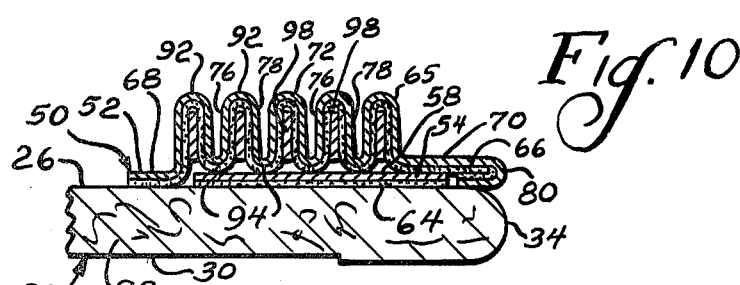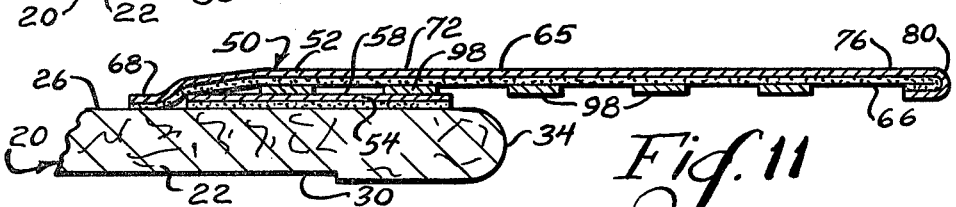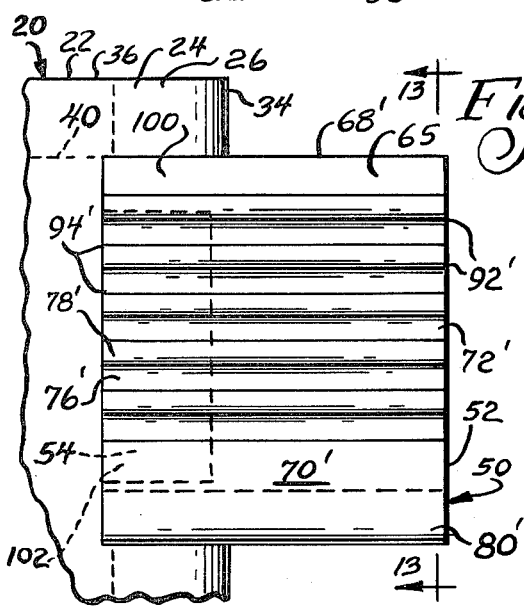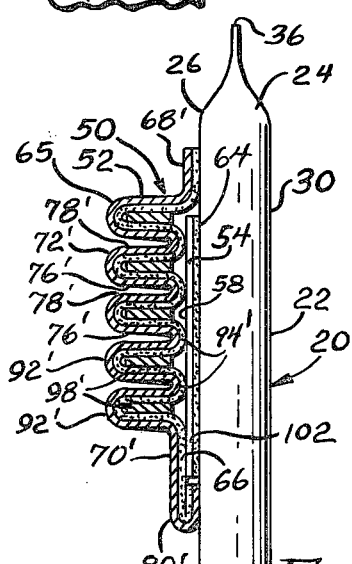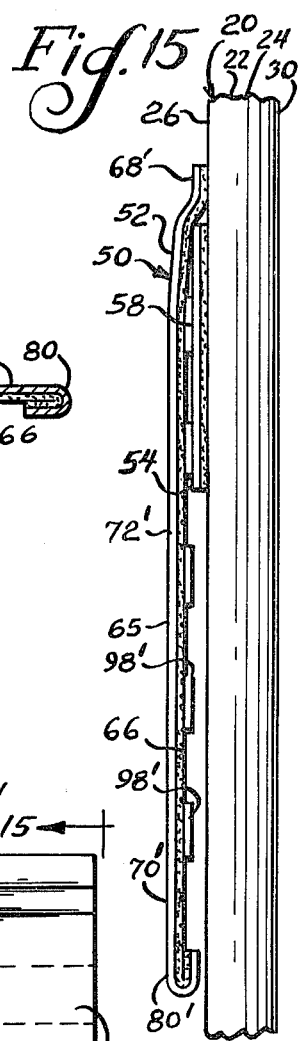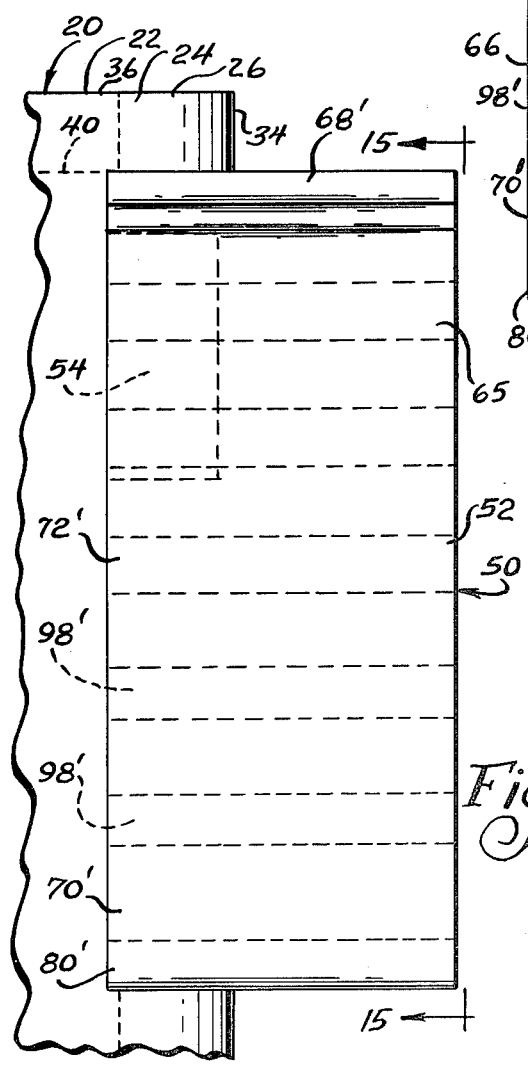

DIAPER WITH EXTENSIBLE FASTENER

This is a continuation, of application Ser. No. 752,495 filed Dec. 20, 1976 now abandoned.

BACKGROUND OF THE INVENTION

The present invention relates to absorbent articles, and more particularly to disposable diapers.

A various assortment of disposable diapers have been proposed for use on infants, and have become increasingly popular with parents since they may be discarded after a single use and need not be laundered. Such diapers are normally constructed having a fluid impervious backing sheet, a fluid pervious top or cover sheet, and an absorbent pad intermediate the backing and cover sheets.

Many of the diapers have been provided with tape fasteners which are used to secure the diaper about the infant. Such fasteners generally take the form of a pressure-sensitive tape strip having a first end attached to the diaper and a second securement end which is attached to the diaper during placement. Prior to use, adhesive on the securement end must be covered to prevent premature contact of the adhesive against the diaper or other article. Hence, in one form, the fasteners have been provided with separate release sheets which cover the adhesive on the securement ends. However, this form of tape fastener has been found lacking in that the release sheets must be discarded when removed at the time of diaper placement, thus causing inconvenience to the parents. In an alternative form, the separate release sheets have been anchored to the front surface of the diaper itself, and the securement ends are peeled from the release sheets during placement of the diaper, after which the first ends of the tape strips, which are attached to the back surface of the diaper, retain the tape strips to this portion of the diaper. Of course, an overriding consideration in construction of the diaper is the cost of manufacture, since the diaper must be inexpensive to the consumer due to its disposability. The manufacturing equipment required to place the alternative fastener on the diaper is unduly complex, thus adding to the cost of the diaper, since the release sheet must be placed on the front surface of the diaper, the first end of the tape strip must be attached to the back surface of the diaper, and the securement end of the tape strip must be folded around a side edge of the diaper and attached to the release sheet.

SUMMARY OF THE INVENTION

A principal feature of the present invention is the provision of a disposable diaper having a tape fastener of simplified construction and reduced cost.

The diaper of the present invention comprises, an absorbent pad assembly having opposed surfaces, and at least one side edge. The diaper has a tape fastener comprising, release sheet means on one of the surfaces of the pad assembly adjacent the side edge, and tape means having a first portion secured to the one surface of the pad assembly, a securement portion releasably attached to the release sheet means, and an extensible portion connecting the first and securement portions.

A feature of the present invention is that the securement portion may be removed from the release sheet means and the extensible portion permits extension of the securement portion past the side edge to secure the diaper about an infant.

Thus, a feature of the invention is that the tape means may be readily extended to a position for securing the diaper about the infant thus facilitating placement of the diaper.

A further feature of the invention is that the tape means may be extended after overlapping the diaper side margins during placement, thus eliminating the inconvenience of premature release sheet removal and minimizing the possibility that exposed adhesive may be inadvertently adhered to the wrong location or rendered inoperative when otherwise exposed with the diaper margins separated.

Another feature of the invention is that the release sheet means and tape means are attached to the same surface of the diaper during manufacture, thus simplifying the manufacturing procedures and reducing the cost of the diaper.

A further feature of the invention is that in embodiments of the fastener the tape means does not extend past the diaper side edge, thus facilitating packaging of the diaper.

Yet another feature of the invention is that the release sheet means remains attached to the diaper and eliminates the necessity for discarding separate release sheets during placement of the diaper.

Still another feature of the invention is that in an embodiment the tape means may be laterally extended to increase the surface area of the tape means which is attached to another portion of the diaper during placement.

Further features will become more fully apparent in the following description of the embodiments of this invention and from the appended claims.

DESCRIPTION OF THE DRAWINGS

In the drawings:

FIG. 1 is a fragmentary back plan view of a disposable diaper having a tape fastener of the present invention;

FIG. 2 is a fragmentary sectional view taken substantially as indicated along the line 2—2 of FIG. 1 and showing the tape fastener in a folded configuration on a back surface of the diaper;

FIG. 3 is a fragmentary sectional view of the diaper of FIG. 1 showing the tape fastener in a partially unfolded configuration;

FIG. 4 is a fragmentary sectional view of the diaper of FIG. 1 showing the tape fastener in an unfolded configuration for use in securing the diaper about an infant;

FIG. 5 is a fragmentary sectional view of a diaper showing another embodiment of the tape fastener of the present invention;

FIG. 6 is a fragmentary sectional view of a diaper showing another embodiment of the tape fastener of the present invention;

FIG. 7 is a fragmentary sectional view of a diaper showing another embodiment of the tape fastener of the present invention;

FIG. 8 is a fragmentary sectional view of a diaper showing another embodiment of the tape fastener of the present invention;

FIG. 9 is a fragmentary sectional view showing the tape fastener of FIG. 8 in an extended configuration;

FIG. 10 is a fragmentary sectional view of a diaper showing another embodiment of the tape fastener of the present invention;

FIG. 11 is a fragmentary sectional view showing the tape fastener of FIG. 10 in an extended configuration;

FIG. 12 is a fragmentary back plan view of a diaper showing another embodiment of the tape fastener of the present invention;

FIG. 13 is a fragmentary sectional view taken substantially as indicated along the line 13—13 of FIG. 12;

FIG. 14 is a fragmentary back plan view of the diaper of FIG. 12 showing the tape fastener in an extended configuration; and FIG. 15 is a side view taken substantially along the line 15—15 of FIG. 14.

DESCRIPTION OF THE PREFERRED EMBODIMENTS

Referring now to FIGS. 1 and 2, there is shown a disposable diaper generally designated 20 having an absorbent pad assembly 22. The pad assembly 22 has a fluid impervious backing sheet 24, such as polyethylene, defining a back surface 26 of the pad assembly, a fluid pervious cover or top sheet 28, such as a nonwoven material, defining a front surface 30 of the pad assembly 22, and an absorbent pad 32, such as comminuted wood pulp termed in the art as fluff, located intermediate the backing sheet 24 and cover sheet 28. The pad assembly 22 has a pair of side edges 34, and a pair of end edges 36 connecting the side edges 34. The absorbent pad 32 also has a pair of side edges 38 and end edges 40 connecting the side edges 38. In a preferred form, as shown, the side edges 38 of the pad 32 are located adjacent the side edges 34 of the pad assembly 22, and the fluid impervious backing sheet 24 has lateral side margins 42 folded over and secured to the top sheet 28, such that the backing sheet side margins 42 cover lateral side margins of the absorbent pad 32.

The diaper 20 has a pair of tape fasteners generally designated 50 having a pressure-sensitive tape strip 52 and a release sheet 54, with each of the fasteners being located adjacent a side edge 34 of the pad assembly 22. The release sheet 54 has an inner surface 56, an outer release surface 58, a first segment 60, and a second segment 62 extending from an inner end of the first segment 60. The release sheet 54 may be made from any suitable material, such as paper or polyethylene, and the outer release surface 58 of the paper release sheet may be formed by a suitable silicone treatment or coating. As shown, the inner surface 56 of the first segment 60 is attached to the back surface 26 of the pad assembly 22 adjacent the side edge 34 by suitable means, such as adhesive 64.

The tape strip 52 has a relatively inextensible backing 65, such as paper, adhesive 66 on a front surface of the backing 65, a first end portion 68 secured to the back surface 26 of the pad assembly by the adhesive 66, a securement end portion 70 remote the first portion 68 and having its adhesive 66 releasably attached to the outer release surface 58 of the first release sheet segment 60, and an extensible central portion 72 extending between and connecting the first end portion 68 and securement end portion 70. As shown, the central portion 72 of the tape strip 52 has a fold about a laterally extending fold line 74 defining a first section 76 extending between the fold line 74 and first end portion 68 of the tape strip 52, and a second section 78 extending between the fold line 74 and the securement end portion 70 of the tape strip 52. The inner surface 56 of the release sheet second segment 62 has a relatively high affinity for the adhesive 66 on the tape strip 52, and the inner surface 56 of the second segment 62 is fixedly attached to the adhesive 66 on the first section 76 of the central portion 72. Also, the adhesive 66 on the second section 78 of the central portion 72 is releasably attached to the outer release surface 58 of the second release sheet segment 62. As shown, the securement portion 70 of the tape strip 52 may have a folded over end defining a tab 80 to facilitate removal of the tape strip from the release sheet.

With reference to FIGS. 1 and 2, the tape fastener 50 is shown in a folded configuration on the back surface 26 of the pad assembly 22 prior to use of the diaper, with the tape strip 52 being releasably attached to the outer release surface 58 of the release sheet 54. In use, the tab 80 may be grasped in order to peel the securement portion 70 and second section 78 of the tape strip 52 from the release surface 58 of the release sheet 54, as shown in FIG. 3, such that the securement portion 70 of the tape strip 52 is drawn past the side edge 34 of the pad assembly 22 while the first and second release sheet segments 60 and 62 fold about a central fold line 81 of the release sheet. When the outer end of the tape strip has been fully extended past the side edge 34, as shown in FIG. 4, the release surface 58 of the release sheet segments 60 and 62 has been folded together, and the securement portion 70 of the tape strip 52 is located at a position for attaching the tape strip to another portion of the diaper during placement on an infant.

In this manner, the tape strip 52 may be readily removed from the release sheet 54 and extended into a configuration for use in securing the diaper. Also, both the tape strip 52 and release sheet 54 are secured to the back surface of the diaper, thus eliminating the necessity of securing parts of the tape strip and release sheet on opposed surfaces of the diaper, which requires folding of the tape strip around a side edge of the diaper, and simplifying the manufacturing procedures in order to reduce the cost of the diaper. In the folded configuration, the strip does not extend past the diaper side edge, and facilitates packaging of the diaper. Further, the release sheet 54 remains anchored to the diaper after unfolding the tape strip for use, thus eliminating the necessity of discarding separate release sheets during placement of the diaper. Of course, it will be understood that a similar tape fastener is located adjacent the opposed side edge of the diaper, as well as in the other embodiments of the tape fastener, described below.

Another embodiment of the diaper of the present invention is illustrated in FIG. 5, in which like reference numerals designate like parts. In this embodiment, the release sheet 54 is spaced a sufficient distance from the side edge 34 of the pad assembly 22, such that the adhesive 66 on the second section 78 of the central portion 72 is attached to the back surface 26 of the pad assembly 22 when the tape strip 52 is unfolded from the release sheet and extended past the side edge 34 of the pad assembly 22. Thus, the adhesive 66 on the tape strip 52 retains the tape strip against the back surface 26 of the pad assembly 22 at a location intermediate the release sheet 54 and the side edge 34 of the pad assembly 22. In other respects, the tape fastener 50 of FIG. 5 operates in the manner previously described in connection with the fastener of FIGS. 1-4.

Another embodiment of the diaper of the present invention is illustrated in FIG. 6, in which like reference numerals designate like parts. In this embodiment, the first section 76 of the central portion 72 has an adhesive free inner surface 82 which is treated to have a relatively slight affinity for the adhesive 66 on the second section 78 of the central portion 72. Thus, the adhesive 66 on the second section 78 is releasably attached to the release surface 82 of the first section 76, such that the second section 78 may be peeled from the first section 76 when the tape strip is unfolded and extended past the side edge 34 of the pad assembly 22. Accordingly, the release surface 82 of the first section 76, which faces the second section 78, replaces the second segment 62 of the release sheet 54 described in connection with the tape fastener of FIGS. 1–4. In other respects, the tape fastener of FIG. 6 operates in a manner similar to that described in connection with the tape fastener of FIGS. 1–4.

Another embodiment of the diaper of the present invention is illustrated in FIG. 7, in which like reference numerals designate like parts. In this embodiment, the inner surface 82 of the first strip section 76 and the inner surface 84 of the second strip section 78 are both free of adhesive. Thus, the first and second sections 76 and 78 of the central strip portion 72 are free of attachment. During use, the securement portion 70 of the tape strip 52 is removed from the release surface 58 of the release sheet 54, after which the tape strip is extended past the side edge 34 of the pad assembly 22 in a manner as previously described.

Another embodiment of the diaper of the present invention is illustrated in FIGS. 8 and 9, in which like reference numerals designate like parts. In this embodiment, with reference to FIG. 8, the release sheet 54 has a first end 86 secured to the back surface 26 of the pad assembly 22 adjacent the side edge 34 by adhesive 64, a second inner end 88 secured to the back surface 26 of the pad assembly 22 adjacent the first portion 68 of the tape strip 52 by adhesive 64', and a central section 90 extending between the ends 86 and 88 of the release sheet 54. The outer release surface 58 of the central section 90 is releasably attached to the adhesive 66 on the central strip portion 72. As shown, the central section 90 of the release sheet 54 and the central portion 72 of the tape strip 52 are fan or accordion folded along a plurality of outer lateral fold lines 92 and inner lateral fold lines 94 intermediate the fold lines 92 in order to define a folded configuration of the tape fastener 50 of reduced longitudinal dimensions in the region of the central section 90 and central portion 72. The outer fold lines 92 and adjacent inner fold lines 94 define adjacent pairs of first and second strip sections 76 and 78 intermediate the fold lines. The tape fastener may also have spots of adhesive 96 retaining the inner surface 56 of the release sheet central section 90 to the back surface 26 of the pad assembly 22 adjacent the inner fold lines 94. In this manner, as shown in FIG. 8, the tape fastener is maintained in the folded configuration of reduced longitudinal dimensions prior to placement of the diaper. In use, with reference to FIGS. 8 and 9, the tab 80 is grasped and the tape strip 52 is peeled from the release sheet 54 while extending the securement portion 70 past the side edge 34 of the pad assembly 22. In this manner, the tape strip slides from the release surface 58 of the release sheet 54 while the outer end of the tape strip 52 is pulled past the side edge 34 of the pad assembly 22, and, as shown in FIG. 9, the release sheet 54 remains anchored to the back surface 26 of the pad assembly 22. In this configuration, the securement portion 70 of the tape strip 52 extending past the side edge 34 of the pad assembly 22 is suitably positioned for securing the diaper about an infant.

Another embodiment of the diaper of the present invention is illustrated in FIGS. 10 and 11, in which like reference numerals designate like parts. With reference to FIG. 10, in this embodiment the release sheet 54 is secured to the back surface 26 of the pad assembly 22 by adhesive 64 adjacent the side edge 34 of the pad assembly 22, and the adhesive 66 of the securement portion 70 is releasably attached to the outer release surface 58 of a release sheet end nearest the side edge 34 of the pad assembly 22. As before, the central portion 72 of the tape strip 52 is fan or accordion folded along a plurality of outer lateral fold lines 92 and inner lateral fold lines 94 intermediate the fold lines 92, such that the fold lines 92 and 94 define adjacent first and second sections 76 and 78 of the central strip portion 72, as previously described. However, in this embodiment the fastener 50 has a plurality of separate release sheet segments 98 interposed between the adjacent pairs of first and second strip sections 76 and 78. In a preferred form, one of the opposed surfaces of the segments 98 has a relatively slight affinity for the adhesive 66 on the tape strip 52 and constitutes a release surface, while the other opposed surfaces of the segments 98 have a relatively high affinity for the adhesive 66. In a preferred form, the release surfaces face toward the second sections 78 of the central strip portion 72. Also, as shown, the release sheet 54 may extend from the side edge 34 of the pad assembly 22 toward the first portion 68 of the tape strip 52, such that the adhesive 66 of the central strip portion 72 adjacent the inner fold lines 94 is releasably attached to the outer release surface 58 of the release sheet 54.

Accordingly, the release sheet segments 98 are releasably attached to one of the sections 76 or 78 of the central strip portion 72, while the other surfaces of the segments 98 are fixedly attached to the adhesive on the adjacent section 78 or 76. Also, as previously indicated, the adhesive 66 on the securement portion 70 is releasably attached to the release surface 58 of the release sheet 54. In this manner, the tape strip is retained in a folded configuration of reduced longitudinal dimensions prior to use of the diaper on the back surface thereof. In use, the tab 80 is grasped in order to pull the securement portion 70 of the tape strip 52 past the side edge 34 of the pad assembly 22, while the release surfaces of the release sheet segments 98 are peeled from the adhesive 66 of the associated strip sections. In this manner, the tape strip may be extended past the side edge 34 of the pad assembly 22, as shown in FIG. 11, into a configuration such that the outer portion of the tape strip 52 may be utilized to secure the diaper about an infant.

It will be apparent that numerous variations of the tape fastener are within the scope of the present invention. For example, separate release segments, as discussed in connection with FIGS. 10 and 11, may be utilized in the fastener of FIGS. 1–4. Also, any of the fasteners may be spaced from the side edge 34 of the pad assembly 22, in a manner similar to that described in connection with FIG. 5. Of course, the release sheet segments 98 of FIGS. 10 and 11 may be omitted in a fan-folded tape strip through use of spaced release coatings on an inner surface of the tape strip, as discussed in connection with FIG. 6, e.g., alternate adhesive and release zones may be utilized in the fastener of FIGS. 10 and 11. In an alternative form of FIGS. 8–11, portions of the inner surface of the tape strip in a fan-folded configuration may be free of adhesive, as discussed in connection with FIG. 7. Similarly, the central portion 72 of the tape strip 52 in the embodiment of FIGS. 8 and 9 may have a single fold, such as shown in FIG. 2, in order that the release sheet in the fastener of FIGS. 1-4 would have opposed ends anchored adjacent the first strip portion 68 and adjacent the side edge 34 of the pad assembly 22.

Another embodiment of the diaper of the present invention is illustrated in FIGS. 12-15, in which like reference numerals designate like parts. With reference to FIGS. 12 and 13, in this embodiment the tape fastener 50 has a tape strip 52 and a release sheet 54. The tape strip 52 has a first longitudinally extending side portion 68' having an inner end 100 secured to the back surface 26 of the pad assembly 22 adjacent the side edge 34 of the pad assembly. The release sheet 54 is secured by adhesive 64 to the back surface 26 of the pad assembly 22 adjacent the side edge 34 of the pad assembly 22, and the release sheet 54 has an outer release surface 58. The tape strip 52 has a second longitudinally extending side portion 70' remote the first side portion 68', with adhesive 66 of the tape strip on the side portion 70' being releasably attached to the release surface 58 of the release sheet 54 adjacent an end 102 of the release sheet 54. The tape strip may have a folded over side defining a tab 80' adjacent the side portion 70' of the tape strip 52.

The tape strip 52 has a plurality of longitudinally extending outer fold lines 92' and a plurality of longitudinally extending inner fold lines 94' intermediate the fold lines 92' defining a fan or accordion folded configuration of a lateral central portion 72' of the tape strip 52. The fold lines 92' and 94' define first and second longitudinally extending adjacent sections 76' and 78' intermediate the respective fold lines 92' and 94'. Also, the fastener 50 has a plurality of release sheet segments 98' interposed between the adjacent sections 76' and 78' of the central strip portion 72'. In a preferred form, one of the opposed surfaces of the segments 98' constitutes a release surface, while the other opposed surfaces of the segments 98' have a relatively high affinity for the adhesive 66 on the tape strip 52. As shown, the adhesive 66 of the tape strip 52 adjacent the fold lines 94' may be releasably attached to the release surface 58 of the release sheet 54.

In this manner, the release sheet 54 and the release sheet segments 98' retain the tape strip 52 in a folded configuration of reduced lateral dimensions prior to use of the diaper. In use, the tab 80' of the tape strip 52 is grasped and the tab 80' is pulled in a direction away from the end edge 36 of the pad assembly 22, such that the adhesive 66 of the tape strip 52 is peeled from the release surface 58 of the release sheet 54 and from the release surfaces of the release sheet segments 98'. Accordingly, the tape strip 52 may be unfolded into a configuration of enlarged lateral dimensions, as shown in FIGS. 14 and 15, such that the laterally extended tape strip 52 may be attached to an increased region of the diaper during placement in order to obtain a film securement between the strip securement portion and diaper. Of course, with reference to FIG. 15, the adhesive 66 on the extended inner portion of the tape strip may be secured to the back surface 26 of the pad assembly 22 in the region underlying this portion of the tape strip 52.

In an alternative form, the tape fastener 50 of FIGS. 12-15 may utilize a single release sheet, as discussed in connection with FIGS. 8 and 9, while permitting lateral extension of the tape strip during placement of the diaper. Also, the fastener of FIGS. 12-15 may have a single lateral fold, in a manner discussed in connection with the longitudinally folded fastener of FIGS. 1-4, alternate zones of adhesive and release surfaces may be utilized on the tape strip in the fastener of FIGS. 12-15, as discussed in connection with FIG. 6, or adhesive-free zones of the strip may be utilized in the fastener of FIGS. 12-15, as discussed in connection with the fastener of FIG. 7. Thus, the fastener of FIGS. 1-5 may be used in a configuration permitting lateral extension of the tape strip. Further, the fastener of FIGS. 12-15 may be free of adhesive adjacent the inner fold lines 94'.

The foregoing detailed description is given for clearness of understanding only, and no unnecessary limitations should be understood therefrom, as modifications will be obvious to those skilled in the art.

I claim:
1. A disposable diaper, comprising:
an absorbent pad assembly having opposed surfaces, and a side edge; and
a tape fastener comprising, release sheet means on one of said surfaces of the pad assembly adjacent said side edge, and tape means having a first portion secured to said one surface of the pad assembly, a securement portion releasably attached to said release sheet means, and an extensible portion connecting said first and securement portions, said securement portion being removed from the release sheet means and said extensible portion permitting extension of said securement portion past said side edge to secure the diaper about an infant, said extensible portion comprising a central portion of the tape means having at least one fold, and said release sheet means comprising a release sheet having a release suface releasably attached to adhesive on said central portion, a first end segment attached to said one surface of the pad assembly adjacent said side edge, and a second segment attached to the diaper adjacent said first portion of the tape means, said release sheet means being spaced sufficiently from said side edge to permit attachment of adhesive on the extensible portion against said one surface of the pad assembly.

2. The diaper of claim 1 wherein said central portion has a plurality of folds.

3. A disposable diaper, comprising:
an absorbent pad assembly having a pair of opposed surfaces, and a side edge; and
a tape fastener comprising, a pressure-sensitive tape strip having a first portion attached to one of said surfaces of the pad assembly, a securement portion remote the first portion, and an extensible central portion extending between the first and securement portions, said fastener having a release sheet having a first end attached to said one surface of the pad assembly adjacent said side edge, a second end attached to the diaper adjacent said first strip portion, and an outer release surface, with adhesive on said central strip portion being releasably attached to the release surface of the release sheet intermediate said first and second ends, and said central strip portion and attached release sheet having at least one lateral fold at a location intermediate the first and second ends of the release sheet.

4. The diaper of claim 3 wherein said central strip portion and attached release sheet have a plurality of lateral folds intermediate the first and second ends of the release sheet, with said release sheet releasably retaining the central strip portion in a folded configuration of reduced longitudinal dimensions between the first and second ends of the release sheet.

5. The diaper of claim 3 wherein said central strip portion and attached release sheet are accordion-folded intermediate the first and second ends of the release sheet.

6. A disposable diaper, comprising:
- an absorbent pad assembly having opposed surfaces, and a side edge; and
- a tape fastener comprising, a pressure-sensitive tape strip having an end portion attached to one of said surfaces of the pad assembly and a second portion extending from the first portion, and a release sheet having an outer release surface releasably attached to adhesive on the second strip portion, said second strip portion and release sheet having a plurality of outer lateral fold lines and a plurality of inner lateral fold lines defining a folded configuration of the second strip portion and release sheet of reduced longitudinal configuration, with an end of the release sheet remote the first strip portion being attached to said one surface of the pad assembly with the second strip portion and release sheet in said reduced configuration, and with an inner surface of the release sheet being attached to said one surface of the pad assembly adjacent said inner fold lines.

* * * * *